US006404494B1

(12) United States Patent
Masonis et al.

(10) Patent No.: US 6,404,494 B1
(45) Date of Patent: Jun. 11, 2002

(54) MEASUREMENT OF THE LIDAR RATIO FOR ATMOSPHERIC AEROSOLS USING A 180 DEGREE-BACKSCATTER NEPHELOMETER

(75) Inventors: Sarah J. Masonis; Theodore L. Anderson; Robert J. Charlson, all of Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/470,576

(22) Filed: Dec. 22, 1999

Related U.S. Application Data

(60) Provisional application No. 60/113,971, filed on Dec. 22, 1998.

(51) Int. Cl.$^7$ .............................................. G09N 21/00
(52) U.S. Cl. ....................... 356/338; 356/339; 356/340; 356/342; 356/441; 356/442; 250/574; 250/575
(58) Field of Search ................................. 356/335–443, 356/497, 138, 445

(56) References Cited

U.S. PATENT DOCUMENTS

| | | | | |
|---|---|---|---|---|
| 3,700,333 A | * | 10/1972 | Charlson et al. | 356/338 |
| 3,973,848 A | * | 8/1976 | Kowett et al. | 250/345 |
| 4,072,424 A | * | 2/1978 | McMullan et al. | 250/573 |
| 4,375,334 A | * | 3/1983 | Gerber | 356/339 |
| 4,871,251 A | * | 10/1989 | Priekschat et al. | 356/336 |
| 5,604,590 A | * | 2/1997 | Cooper et al. | 356/338 |

OTHER PUBLICATIONS

Rosen, James M. and Kjome, Norman T. "Backscattersconde: a new instrument for atmospheric aerosol research." Applied Optics, vol. 30, No. 12, Apr. 20, 1991, pp. 1552–1561.
Rosen, James M. and Kjome, Norman T. "Balloon–borne measurements of the aerosol extinction–to–backscatter ratio." Journal of Geophysical Research, vol. 102, No. D10. May 27, 1997. pp. 11.165–11.169.
Rosen, James. M., Pinnick, Ronald G., and Garvey, Dennis M. "Measurement of extinction–to–backscatter ratio for near–surface aerosols." Journal of Geophysical Research, vol. 102, No. D5, Mar. 20, 1997. pp. 6017–6024.
Rosen, James. M., Kjome, Norman T., and Liley, J. B. "Tropospheric aerosol backscatter at a midlatitude site in the northern and southern hemispheres." Journal of Geophysical Research, vol. 102, No. D17, Sep. 20, 1997. pp. 21.321–21.339.

* cited by examiner

Primary Examiner—Frank G. Font
Assistant Examiner—Sang H. Nguyen
(74) Attorney, Agent, or Firm—Ronald M. Anderson

(57) ABSTRACT

An integrating nephelometer is modified to measure 180° backscattering from an aerosol. A laser is mounted outside a housing of the nephelometer and produces a coherent light beam that is directed into a sample volume of the nephelometer, substantially along an optical sensing axis (<4° off the optical axis). Light from the laser beam that is reflected by an aerosol travels back along the optical sensing axis toward a photomultiplier tube (PMT) light detector, which thus produces a signal indicative of the backscattering from the aerosol. A portion of the laser beam is conveyed into the housing of the nephelometer through an optical fiber for use as a reference beam. A motor-driven chopper disk disposed across the optical axis is divided into an open sector, a calibration sector (with a very low transmission), and a flat black light absorbing sector. During a calibration mode to monitor the stability of the laser, the calibration sector diffuses the reference beam so that only a portion of it is measured by the PMT detector. A background noise of the PMT detector is measured when light is blocked by the flat black light absorbing sector. The latter two measurements are used to correct the backscattering measurement for the aerosol. A lidar ratio of the aerosol is determined as a function of the backscattering measurement, a measurement of light extinction due to total light scattering by the aerosol, and a measurement of its light absorption.

14 Claims, 4 Drawing Sheets

Figure 1:
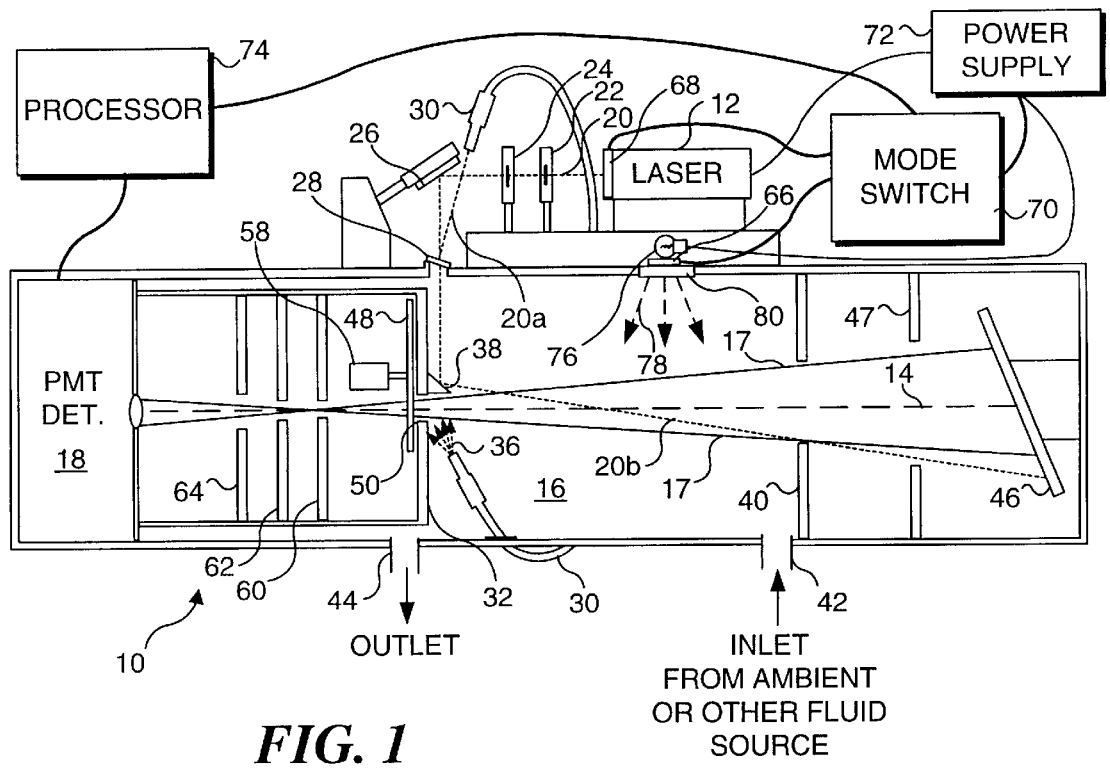

MEASUREMENT OF THE LIDAR RATIO FOR ATMOSPHERIC AEROSOLS USING A 180 DEGREE-BACKSCATTER NEPHELOMETER

RELATED APPLICATIONS

This application is based on prior copending provisional patent application Ser. No. 60/113,971, filed on Dec. 22, 1998, the benefit of the filing date of which is hereby claimed under 35 U.S.C. § 119(e).

FIELD OF THE INVENTION

The present invention generally relates to a method and apparatus for monitoring aerosols or particulates in a fluid, and more specifically, to a method and apparatus for monitoring the lidar ratio for particulates or aerosols in the atmosphere.

BACKGROUND OF THE INVENTION

A recent National Research Council panel report summarizes six independent lines of evidence supporting the hypothesis that direct (i.e., clear-sky) climate forcing due to the scattering and absorption of sunlight by anthropogenic aerosols is a major factor in global climate change. Visibility is similarly known to depend on scattering and absorption of light by atmospheric aerosols. A variety of aerosol measurements (as well as theoretical models) contribute to this evidence, but notably lacking is a physically meaningful contribution from elastically scattering lidar. Nevertheless, the potential contribution of this technology is enormous, given its exquisite precision, vertical resolution, and the relative ease of data acquisition. This potential has yet to be exploited because of difficulties in quantitatively and accurately relating the elastically scattered lidar signal to the aerosol parameters relevant to climate forcing and visibility.

Analogous to radar but operating at shorter wavelengths, a lidar instrument transmits pulsed laser radiation and measures what is backscattered by gases, particles, or other objects in the atmosphere. The return time of the signal corresponds to distance from the transmitter such that range-dependent information is acquired. The intensity of the signal depends on two quantities: (1) how effectively the laser radiation is backscattered at a specific location in the atmosphere; and, (2) how effectively the laser radiation is extinguished by the intervening atmosphere. Interpreting the lidar signal depends on an ability to separate these two quantities—local 180° backscatter and optical depth over the entire range. It is this deconvolution of local backscatter and range-dependent optical depth, which is at the heart of the lidar retrieval challenge.

Following instrument calibration, a vertically pointing lidar provides a direct measurement of the quantity S(z), characterized by the following equation:

$$S(z) = A\beta(z)\exp\left[-2\int_{z_L}^{z}\sigma_e(z')dz\right] = A\beta(z)\exp[-2\tau(z_L, z)] \quad (1)$$

where A is an instrumental calibration constant, $\beta(z)$ is the 180° backscatter coefficient ($m^{-1}sr^{-1}$) from both molecules and aerosols at height z(m), $\sigma_e$ is the extinction coefficient ($m^{-1}$) from both molecules and aerosols at height z, and $\tau(z_L,z)$ is the extinction optical depth between the lidar height, $z_L$, and z. Equation 1 shows that the fundamental challenge of converting the lidar measurement, S(z), to a geophysically meaningful aerosol quantity is to disentangle $\beta$ and $\tau$— or, equivalently, $\beta$ and $\sigma_e$. Since molecular scattering can be predicted accurately from air density (i.e. temperature and pressure) information, this challenge reduces to disentangling particulate backscattering, $\beta_p$, from particulate extinction, $\sigma_p$. Two types of technologically advanced lidar systems, Raman lidar and high spectral resolution lidar, are able to separate these terms by making auxiliary measurements of the return signal. These instruments are described briefly below.

For lidar systems that detect elastically scattered light only, the quantities $\beta_p$ and $\sigma_{ep}$ can be disentangled if the ratio of the two parameters is known. This quantity is referred to as the lidar ratio, K, $$K(sr) = \frac{\sigma_{ep}}{\beta_p} = \frac{\sigma_{sp} + \sigma_{ap}}{\beta_p} \quad (2)$$

where $\sigma_{sp}$ and $\sigma_{ap}$ are the components of particulate extinction due to light scattering and light absorption, respectively.

Based on Mie calculations that incorporate the ranges of particle size distributions and refractive indices encountered in the troposphere, possible values of K span at least an order of magnitude, from approximately 10 to 100 (sr). The lower values correspond to coarse-particle aerosols like soil .dust and sea salt, while the higher values represent fine particles of smoke and products of gas-to-particle conversion. To explore the sensitivity of lidar-retrieved optical depth to uncertainties in K, we use data from the recent lidar demonstration Shuttle mission (LITE). Table 1 shows the effect on retrieved optical depth of allowing K to vary from 10 to 100. Data consists of two cases when aerosol layers were detected at night over Africa during the LITE mission. The columns labeled $\partial\log\tau_p/\partial\log K$ indicate how a fractional uncertainty in lidar ratio would translate into a fractional uncertainty in optical depth. This sensitivity parameter is seen to vary between the two cases and to be a strong function of lidar ratio. For low K values, K and $\tau_p$ are nearly proportional. For the higher K values (which tend to be characteristic of pollution-derived particles in the sub-$\mu$m size range), the sensitivity is considerably higher—up to a factor of 4. Overall, the factor of ten range of possible lidar ratios translates into a factor of 10 to 40 uncertainty in retrieved optical depth. This range is too large to offer an adequate constraint on lidar retrievals for the problems of climate forcing or visibility.

TABLE 1

| | Case 1* | | Case 2** | |
|---|---|---|---|---|
| K | $\tau_p$ | $\partial\log\tau_p/\partial\log K$ | $\tau_p$ | $\partial\log\tau_p/\partial\log K$ |
| 10 | 0.022 | 1.06 | 0.021 | 1.09 |
| 20 | 0.048 | 1.14 | 0.046 | 1.20 |
| 30 | 0.077 | 1.22 | 0.077 | 1.33 |
| 40 | 0.111 | 1.31 | 0.115 | 1.46 |
| 50 | 0.150 | 1.42 | 0.162 | 1.63 |
| 60 | 0.196 | 1.55 | 0.221 | 1.83 |
| 70 | 0.252 | 1.71 | 0.299 | 2.09 |
| 80 | 0.321 | 1.91 | 0.404 | 2.47 |
| 90 | 0.408 | 2.18 | 0.558 | 3.10 |
| 100 | 0.523 | 2.55 | 0.817 | 4.25 |

*Case 1: Average over 400 records beginning MET 009/01:09:02.60. Aerosol layer extends from 1388 m to 5013 m above sea level.
**Case 2: Average over 300 records beginning MET 009/01:10:32.60. Aerosol layer extends from 1532 m to 5832 m above sea level.

For lack of accurate knowledge of K, most aerosol measurements by elastically scattered lidar are reported as a "scattering ratio" — that is, the ratio of the calibrated signal to the expected signal for particle-free air. This term is useful for qualitative identification of aerosol layers, but not for input into radiative transfer models. The instrument described herein provides a relatively inexpensive method for accurate local measurement of $\beta_p$. When combined with existing instrumentation for measuring $\sigma_{ep}$, this permits an empirical determination of K.

Being small and portable, the new device permits routine ground-based monitoring as well as airborne surveys of $\beta_p$ and K, which will, in turn, allow extensive lidar data sets on tropospheric aerosols to be applied in a quantitative fashion to the aerosol/climate and visibility problems.

The "backscattersonde" described by Rosen and Kjome In "Backscatersonde: a New Instrument for Atmospheric Aerosol Research," Applied Optics, Vol. 30, pp. 1552–1561 (1991) offers a local measurement of $\beta_p$. The backscattersonde is light and inexpensive, and thus well suited for balloon-borne measurements of atmospheric backscatter versus altitude; in contrast, the instrument described herein is currently both too large and too expensive for routine balloon deployment. The backscattersonde has been used to determine the lidar ratio by running it in parallel with a separate instrument that measures scattering and with assumptions about particle absorption.

The backscattersonde has an open sensing volume and a flash lamp light source, so it cannot be calibrated in the laboratory with gases or with particles of known concentration, size and refractive index, and it can only be used at night. The calibrations rely on measurements of air Rayleigh backscattering in the stratosphere in the winter Arctic polar vortex, where particle concentrations are believed to be insignificant. Previous or subsequent measurements in other regions rely on inter-instrument calibration via comparison to reference instruments. However, optical and electronic components may be subject to drift and the resulting uncertainty has not been determined. The instrument senses backscattering over a broad angular range (~160°–179°) and over two broad wavelength ranges centered at 490nm and 700 nm, with bandwidths of about 100 nm. The backscatter at 532 nm is derived by linear interpolation. For these reasons, even for a calibrated system, converting the measured quantity to $\beta_p$ at 532 nm would require an optical model of the instrument and Mie calculations based on assumptions about particle size, refractive index, and sphericity. Thus, the backscattersonde offers a proxy for $\beta_p$ at 532 nm that requires calculations and assumptions that would preferably not be required in an ideal system.

Another technique relevant to measuring aerosol scattering is the Raman lidar method. Molecular and aerosol contributions to light extinction are separated in this. method by measuring Raman-shifted laser light at the appropriate wavelengths for nitrogen, oxygen, carbon dioxide and/or water vapor. Laser light that has been elastically scattered by both molecules and aerosols is also measured. The intensity of the Raman-shifted backscatter from a given altitude depends on $\sigma_{sg}(z)$, $\sigma_{sp}(z)$, and on $\beta_{gas}(z)$, but not on $\beta_p(z)$. The terms $\sigma_{sg}(Z)$ and $\beta_{gas}(Z)$ can be calculated, given an assumed or measured (with a radiosonde) atmospheric density, so inversion yields $\sigma_{sp}(z)$ at the Raman-shifted wavelength. Aerosol extinction at the original laser wavelength is determined from the Raman-shifted signal by using an assumed wavelength-dependence of light scattering, which is based on an assumed size distribution.

To date, this technique has mostly been applied to ultraviolet wavelengths. Because of the strong wavelength dependence of the lidar ratio (according to Mie calculations) for particles below about 10 $\mu$m, lidar ratios measured at ultraviolet (UV) wavelengths with Raman lidar are not directly applicable to visible-wavelength lidar. Conversion to visible wavelengths requires use of an aerosol model (essentially, an assumed aerosol size distribution) that can introduce uncertainties of a factor of two. High spectral resolution lidar (HSRL), like Raman lidar, solves the lidar inversion problem by separating the backscattered light into particulate and molecular components. HSRL takes advantage of the fact that molecules in the atmosphere have much greater Brownian motion than particles, so backscattered light from molecules is wavelength-broadened around the original laser wavelength. An interferometer is used to measure this broadened molecular backscatter. As with the Raman-shifted backscatter described above, the molecular return signal depends on total extinction and gaseous backscatter only, so $\sigma_{sg}(Z)$ can be determined directly, given $\sigma_{sg}(Z)$ and $\beta_{gas}(z)$.

Both the Raman lidar and HSRL are quite expensive and technologically complex. Like other remote or open-air devices (including the backscattersonde), they cannot be calibrated with laboratory particles of known optical properties, and the absolute accuracy of their inversion is difficult to quantify. Independent verification of the measured optical properties is therefore useful. On the other hand, these open-air devices have the enormous advantage of measuring the undisturbed ambient aerosol and can be used to explore vertical variations in the lidar ratio and its sensitivity to ambient relative humidity.

Retrieval of aerosol optical parameters from lidar systems without Raman capability is also possible, given certain assumptions and/or coincident measurements by other instruments. Sun photometers are often used to measure total column optical depth ($\tau$) for vertically pointing lidars. Generally, $\tau$ must be wavelength corrected to the given lidar wavelength. In addition, $\tau$ is measured for the entire atmosphere, whereas the lidar measurement is only over a portion of the atmosphere ($z_L$-z in Equation 1). One approach is to assume that above z the atmosphere is aerosol-free and use a fixed lidar ratio to determine aerosol extinction from the lidar and sun photometer data alone. The sun photometer has been used in conjunction with an optical particle counter (OPC), which determines the ground-level aerosol size distribution for an assumed index of refraction. The aerosol extinction and backscatter—and thus the lidar ratio—are calculated from Mie theory and the OPC data. In these calculations, aerosol optical properties have been considered to be horizontally and vertically homogeneous. It has been assumed that the return signal from the stratosphere is aerosol-free and so, is usable for lidar absolute calibration. However, it is recognized that this approach is invalid after significant volcanic eruptions, because the assumption of an aerosol-free stratosphere is violated.

Another approach employs an aureolemeter, which views forward-scattered sunlight, in conjunction with the sun photometer. The aureolometer gives a columnar averaged size distribution, assuming spherical aerosols with a given index of refraction; this information is useful for Mie calculations of aerosol scattering. An advantage of this method is that forward-scattered radiation is not as sensitive to shape and index of refraction as it is to size, so error in the assumed input parameters is not likely to significantly corrupt the derived size distribution.

Bistatic lidars measure scattered light at a range of angles, providing information on the phase function of the column-averaged aerosol. This data can be used to determine the most probable aerosol index of refraction and size distribution. Mie calculations are then employed to perform the lidar inversion. A ground-based nephelometer has been used with a vertically pointing lidar and calculated lidar ratios by assuming no light absorption and vertical homogeneity of the aerosol. A ground-based nephelometer has been used in conjunction with a bistatic lidar to calculate lidar ratios by assuming no light absorption and vertical homogeneity of the aerosol. Bistatic lidar data have also been inverted using Mie theory with an assumed aerosol size distribution and refractive indices.

Several groups have made measurements of aerosol optical properties in the boundary layer using horizontally. pointing lidars. This measurement is a somewhat easier retrieval problem, in that assumptions of aerosol homogeneity over the lidar optical path are more likely to be accurate. A hard target with fixed optical properties can be used to calibrate a horizontally pointing lidar. Optical properties for a generated aerosol of high optical depth can then be derived using the calibrated lidar. However, the generated particles may not be representative of real atmospheric aerosols. To measure ambient atmospheric aerosols, one group used meteorological data from a lidar site to calculate molecular scattering and an Active Scattering Aerosol Spectrometer Probe (ASASP) to determine the aerosol size distribution at the site. In horizontally homogeneous conditions (i.e., when the lidar signal decreased linearly with range), the lidar ratio could be derived from this data alone. Another group used filter sampling methods and an optical particle counter to determine aerosol size and refractive index, then calculated lidar ratios using Mie theory. Assuming horizontal homogeneity, the system calibration was complete.

All of these approaches to lidar data retrieval require some combination of additional measurements and assumptions about the physical properties of the aerosols. Mie theory is almost always employed to connect these properties to light scattering characteristics, which must be known to retrieve physically meaningful data from the lidar signal. However, Mie theory may inaccurately represent the optical properties of the aerosols, especially if they are non-spherical, even if the input parameters are correct. It would be preferable to employ a direct determination of an aerosol's lidar ratio, to eliminate the need for measurements and assumptions about particle physical properties and subsequent calculation of optical properties and thereby, to improve the accuracy of the result.

SUMMARY OF THE INVENTION

In accord with the present invention, apparatus for measuring a backscatter coefficient for an aerosol entrained in a fluid is defined. The apparatus includes a housing defining a chamber having an inlet port through which a fluid enters the chamber, and an outlet port through which the fluid exits the chamber. An interior of the housing is covered with an optically light absorptive coating that provides minimal light reflection. Disposed within the housing is a light detector, which produces an output signal indicative of an intensity of light incident on the light detector. A plurality of light baffles are disposed between the light detector and the chamber and an optical sensing path of limited scope extending from within the chamber to the light detector. Only light traveling along this optical sensing path toward the light detector is detected by the light detector. A coherent light source produces a beam of coherent light that is directed away from the light detector at an acute angle relative to a central axis of the optical sensing path. The coherent light is reflected from the aerosol within the chamber and the reflected light travels back along the optical sensing path and is detected by the light sensor. Accordingly, the signal produced by the light detector in response to this reflected light is indicative of the backscatter coefficient for the aerosol. Preferably, the acute angle is less than 4°, and more preferably, less than 2°.

The apparatus also preferably includes a rotating chopper disk that has a plurality of sectors with different optical properties, and the sectors are selectively positionable in the optical sensing path. The sectors include an open sector through which light freely travels, a light absorbing sector that blocks and absorbs substantially all light incident upon it, and a calibration sector that transmits only a predefined, relatively small portion of the light incident upon it, diffusing the light that is transmitted over a large area so that only a portion travels along the optical sensing path.

A partially reflecting surface disposed to reflect a portion of the coherent light produced by the coherent light source along a different path than a remainder of the coherent light forms a reference beam. The reference beam is directed toward the chopper disk at an angle so that the reference beam does not travel directly along the optical sensing path toward the light detector when passing through the open sector. When the reference beam is directed at the calibration sector, the diffusion and limited transmission of the reference beam through the calibration sector ensure that only a portion of the reference beam travels toward the light detector along the optical sensing path. This small portion of the reference beam that is detected by the light detector causes the. light detector to produce a signal that is indicative of an intensity of the coherent light source, which is used to compensate for variations in the intensity when determining the backscatter coefficient of the aerosol.

Also included in the apparatus is at least one baffle, disposed within the chamber to prevent light reflected from surfaces of the housing traveling along the optical sensing path toward the light detector. The beam of coherent light is directed toward a light absorption surface, which is disposed within the chamber, so that the beam strikes the light absorption surface at a point outside the optical sensing path, thereby minimizing any reflected light from this surface traveling back toward the light detector along the optical sensing path.

In one embodiment, the apparatus includes a non-coherent light source that is selectively enabled to transmit light into the chamber in a direction generally transverse to the optical sensing path during a time interval when the coherent light source is selectively. disabled from transmitting coherent light into the chamber. Light produced by the non-coherent light source that is reflected from the aerosol toward the light detector along the optical sensing path causes the light detector to produce a signal indicative of light extinction due to total light scattering by the aerosol. In this embodiment, electronically controlled shutters can be disposed between the chamber and both the coherent and non-coherent light sources, to selectively block light produced by the coherent light source and the non-coherent light source during alternate time intervals.

Another aspect of the present invention is directed to a method for measuring a lidar ratio of an aerosol entrained in a fluid. The method includes the step of providing a light detector in a housing through which the fluid and the aerosol are circulated, and a coherent light source. A beam of coherent light produced by the coherent light source is transmitted substantially along an optical sensing path of the light detector, but directed away from the light detector, along a path that deviates from a central axis of the optical sensing path by only a small acute angle. Light scattered by the aerosolparticles back along the optical sensing path is detected by the light detector, producing a signal determinative of light backscatter from the aerosol, at about 180°. In addition, light extinction due to total light scattering by the aerosol is measured, as well as the light absorption of the aerosol. The lidar ratio of the aerosol is then determined as a function of the light backscatter, the light extinction due to total light scattering, and the light absorption by the aerosol.

The lidar ratio is equal to the sum of the light extinction due to scattering and the light absorption of the aerosol divided by the light backscatter of the aerosol.

The small acute angle by which the beam of coherent light deviates from the central axis of the optical sensing path is preferably less than 4°, and more preferably less than 2°. Thus, the signal produced by the light detector is substantially indicative of 180° light backscattering for the aerosol.

BRIEF DESCRIPTION OF THE DRAWING FIGURES

Figure 3:
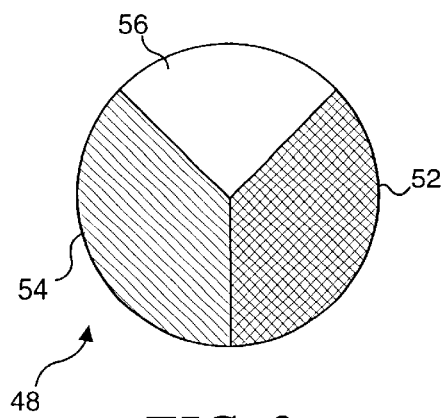
Figure 2A:
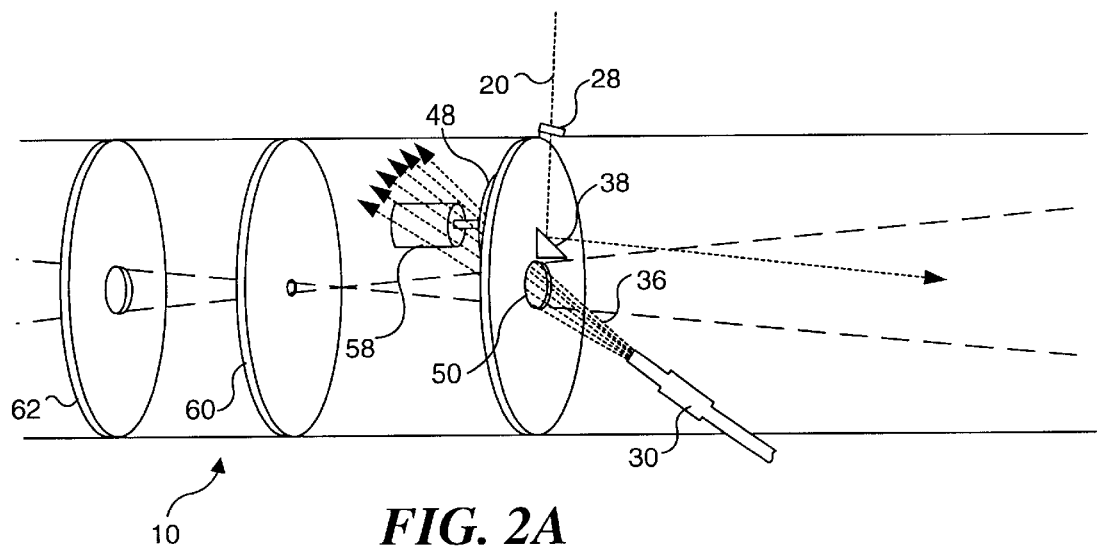
Figure 2B:
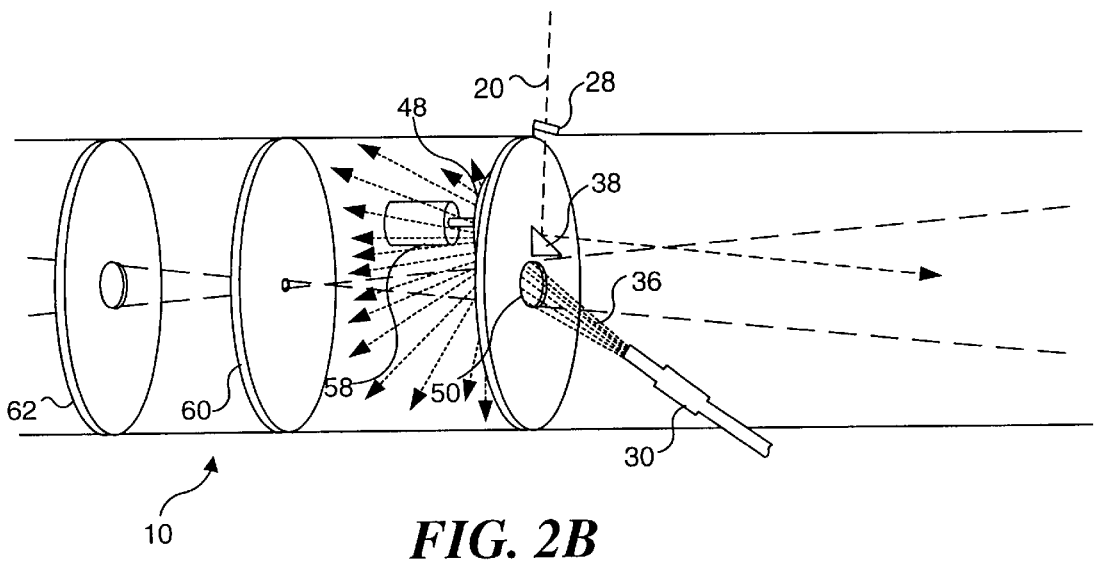
Figure 4A:
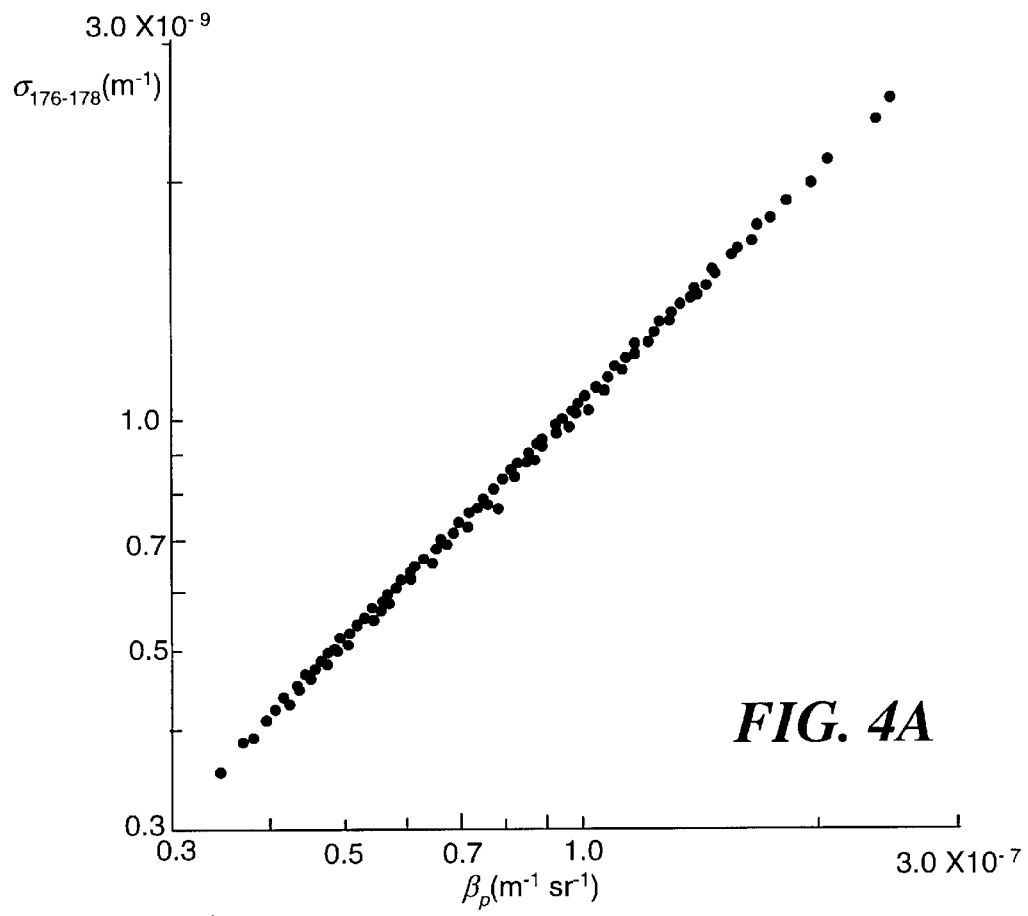
Figure 4B:
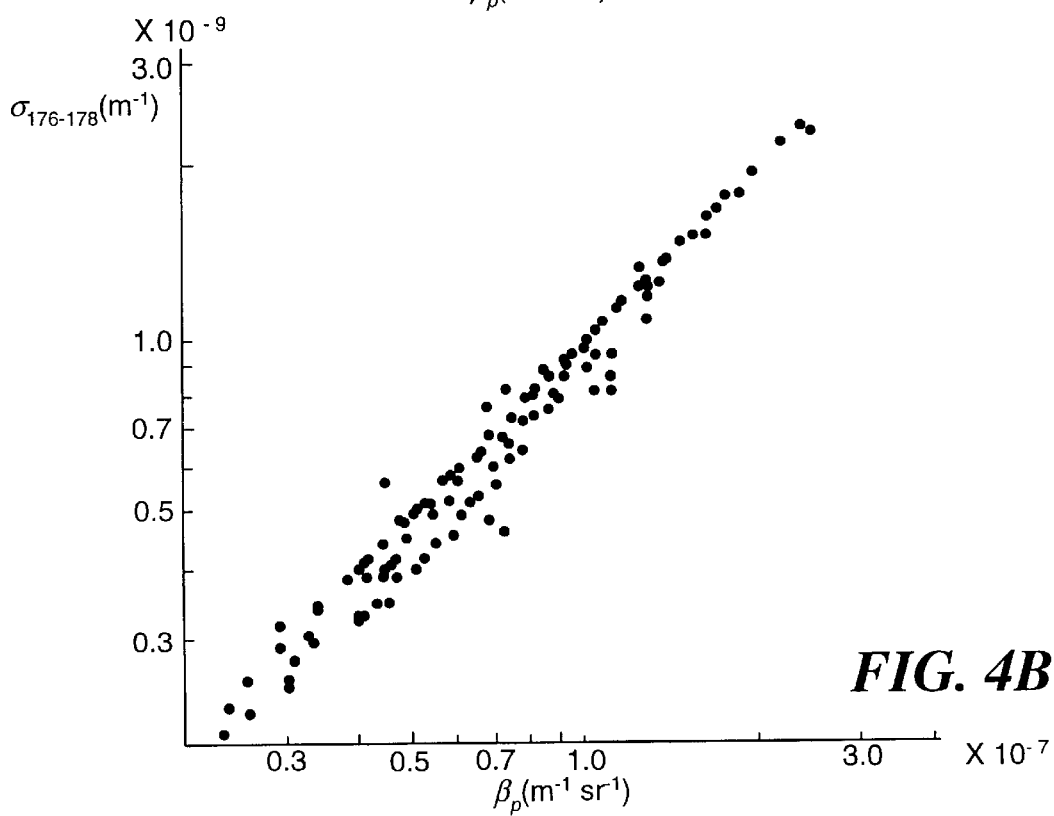
Figure 5:
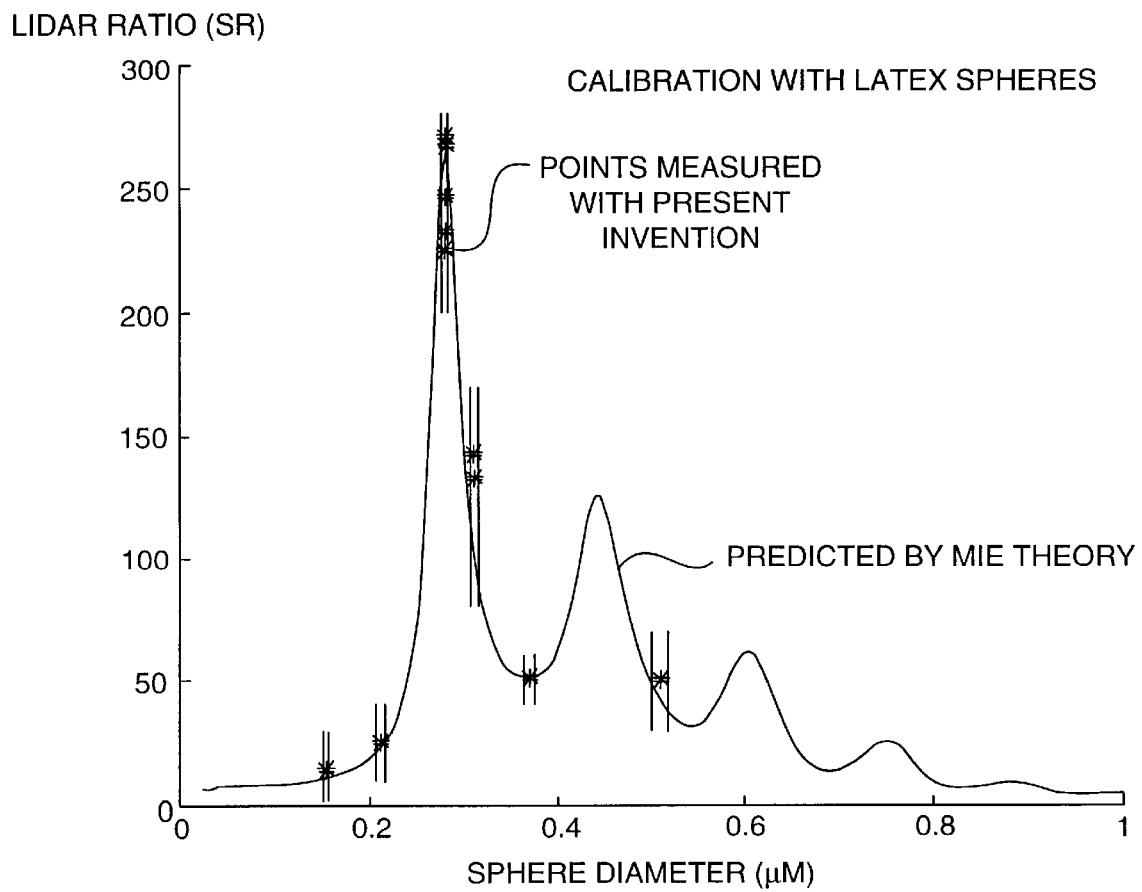

The foregoing aspects and many of the attendant advantages of this invention will become more readily appreciated as the same becomes better understood by reference to the following detailed description, when taken in conjunction with the accompanying drawings, wherein:

FIG. 1 is a schematic diagram illustrating a 180° backscatter nephelometer (vertical scale greatly exaggerated) in accord with the present invention;

FIGS. 2A and 2B respectively illustrate the effect on a reference beam of a chopper disk in a measurement mode and a calibration beam mode;

FIG. 3 schematically illustrates the different sectors of a chopper disk used in the 180° backscatter nephelometer of FIG. 1;

FIGS. 4A and 4B are graphs respectively illustrating the 176°–178° scattering integral sensed by the 180° backscatter nephelometer of FIG. 1, in an accumulation mode and a coarse mode; and FIG. 5 is a graph illustrating the lidar ratio as a function of sphere diameter, as determined with the present invention and as predicted by Mie theory, for various sizes of monodisperse latex spheres.

DESCRIPTION OF THE PREFERRED EMBODIMENT

Instrument Construction

Two technical developments have combined to make a 180° backscatter nephelometer feasible. First is the commercial development and laboratory validation of a high-sensitivity integrating nephelometer by TSI, Inc. (St. Paul, Minn.). This integrating nephelometer performs a geometrical integration of the angular distribution of scattered intensity such that the scattering coefficient of a gaseous or aerosol medium can be measured with the combination of a Lambertian light source and an orthogonal light detector. Two versions of the integrating nephelometer are currently available: the Model 3551, which measures light scattering at one wavelength (550 nm) and the Model 3563, which measures scattering at three wavelengths (450 nm, 550 nm, and 750 nm). The integrating nephelometer (either model) already incorporates several key design features needed for accurate measurement of $\beta_p$.

First, in this device, the scattering volume is enclosed, allowing calibration with gases of known scattering coefficient. Scattering by particle-free air can be measured and subtracted from subsequent measurements of air containing aerosol to derive light scattering due to particles only, $\sigma_{sp}$. Secondly, a reference chopper is used to alternate between measurement of dark counts, the scattering signal, and a reference signal. The system signal is thus corrected for dark count, changes in lamp brightness, and changes in photomultiplier tube sensitivity by using the dark and reference signals. Finally, the temperature and pressure within the sensing volume are continuously monitored, so the amount of scattering coming from air within the sensing volume can be accurately calculated and subtracted from total scattering to determine scattering due to particles only ($\sigma_{sp}$).

The second technological development of import is the commercial production of a diode-pumped laser operating at 532 nm by Uniphase Inc., referred to as a 10 mW MICRO-GREEN™ laser. This laser is more compact and stable than gas lasers operating at similar wavelengths and in accord with the present invention, has been incorporated into the integrating nephelometer to provide an alternate, single-beam source of illumination.

FIG. 1 schematically shows an integrating nephelometer 10 that has been modified in accord with the present invention to measure near-180° backscatter. A laser 12 and associated optics have been added to the integrating nephelometer to produce a collimated beam of light that is aimed very nearly along an optical axis 14 of a nephelometer sample volume 16, pointing away from a photomultiplier tube (PMT) detector 18. With this arrangement, light reaching the detector has either been scattered at near-180° by molecules and particles in the sample volume or it has been scattered off the interior walls. Two lines 17 define an optical sensing path for detector 18, so that only light traveling between these lines (and through their point of intersection if from the sample volume) can be sensed by detector 18. Thus, light reflected from an aerosol particle in sample volume 16 must remain between lines 17 (including their point of intersection) to be sensed by the detector. It should be noted that as used in this description and in the claims that follow, the terms "particles" and "aerosols" in regard to small particulates entrained in a fluid are intended to be interchangeable and synonymous. Thus, for example, a reference to measurements made to determine scattering from aerosols is also intended to apply to scattering from particles, and vice versa.

Laser 12 produces a beam 20 with about a $1/e^2$ diameter of 0.6 mm. The beam is spatially filtered through apertures 22 and 24 and folded by a mirrored surface 26 into the cavity of nephelometer 10 through a window 28. A portion 20a of the beam is reflected from window 28 and enters the end of an optical fiber 30. The optical fiber is guided around the nephelometer and its other end is directed toward a chopper disk 48. The light emitted from the other end of optical fiber 30 is a reference beam 36 for the device. Beam 20 (i.e., the main laser beam) enters the nephelometer perpendicular to optical axis 14, adjacent to a baffle 32, which establishes one end of the scattering or sample volume 16. A small prism 38 with a mirror surface on its hypotenuse and flat black coating on all other sides is mounted on baffle 32 reflects the remaining 99% of beam 20 at a small angle, preferably <4°, e.g., at about an angle of 2.5°, and more preferably <2°, to optical axis 14 (dashed line), producing a beam 20b. (Note that the vertical scale in FIG. 1 has been greatly exaggerated so the angle in the Figure appears considerably larger than stated above.) The prism size is minimized so that beam 20b can be directed as close to the detector field of view as possible. The angular field of view of detector 18 is 1.0°, and the intersection of beam 20b with this field of view defines the sensing volume.

With the geometry in this preferred embodiment of the present invention, light scattered from particles and aerosol within the sample volume at angles between 176.4° and 178.4° is detected by detector 18; however, the angle range can be adjusted by a few degrees. Beam 20b leaves the detector field of view at a baffle 40, restricting the sensing volume to the region between an aerosol inlet 42 and an aerosol outlet 44. The beam terminates at a light dump 46. Baffle 40 and a baffle 47 shield any light reflected from black glass light dump 46 from reaching detectors 18. All surfaces inside the nephelometer, other than active optical surfaces, are coated with black optical paint to minimize stray light scatter. The entire nephelometer volume is sealed against leakage, so that only samples entering via inlet 42 are measured.

Variations in the laser intensity and detector sensitivity are continuously monitored via reference beam 20a. As noted above, a portion of the beam entering the nephelometer volume (e.g., ~1%) is split off at window 28 into beam 20a, which subsequently enters the nephelometer through the optical fiber and is emitted therefrom as reference beam 36. Reference beam 36 is directed through an opening 50 at one end of the sample volume and toward a chopper disk 48.

As shown in FIG. 3, chopper disk 48 is divided into three sectors, including a flat black sector 52 that absorbs almost all of the light incident upon it, a neutral density 4.0 calibration sector 54 that has a 0.0001 transmission coefficient, and an open sector 56 that passes the light traveling through opening 50. Chopper disk 48 is rotatably driven by an electric motor 58 to rotate so that each of the three sectors is selectively positioned behind opening 50, at a desired rotational rate that successively brings each sector into position in front of the opening. As shown in FIG. 2A, when the chopper disk is disposed with open sector 56 behind opening 50, light from the reference beam passes through the opening at an angle and is absorbed by flat black paint that covers the walls of the interior of the nephelometer and largely absorbs the reference beam passing through the open sector. Baffles 60, 62, and 64, which are behind the chopper disk and opening 50, also are painted with optically flat black paint to ensure that the light from the reference beam is absorbed and does not reach detector 18 at this time. It is only light scattered back along the optical axis of the nephelometer that passes through the central openings in these baffles, which reaches detector 18. As shown in FIG. 2B, when chopper disk 48 is in the "calibrate" position with calibration sector 54 positioned behind opening 50, some of the reference beam light strikes the neutral-density coated glass surface of the calibration sector and is redirected toward detector 18. Due to the high sensitivity of the detector, the amplitude of the portion of the reference beam reaching the detector must be limited. The reduction in amplitude of the portion of the reference beam reaching the detector is accomplished by passing the reference beam through the calibration sector of the chopper disk, which has a low transmissivity and diffuses and scatters the reference beam over a large area. Any variations in laser intensity are manifested as changes in the "calibrate" photon counts of detector 18, $C_{cal}$, which are used to calculate the system signal as described below. As a practical matter, it has been determined that the laser used in a preferred embodiment of the present invention is sufficiently stable, so that it is possible to omit the reference beam measurements.

When chopper disk 48 is positioned with flat black background sector 52 disposed behind opening 50, the background noise level of detector 18 can be determined, since there should be virtually no photons incident on the detector at this time. The flat black background sector of the chopper disk effectively blocks all light that passes through opening 50 from reaching the detector. Periodic calibration of the apparatus with gases of known properties can be used determines wall scattering (to be subtracted from the aerosol scattering measured).

Other embodiments are contemplated for providing a reference beam. For example, a reference beam can be derived by using a partially reflecting window disposed in the interior of the nephelometer to redirect a portion of beam 20. This reference beam can be directed into an optical fiber or can be used to illuminate a diffusing surface (not shown) that will direct a portion of the reference beam at the chopper disk. Diffusion of the reference at either the input of the optical fiber or its output has also been implemented. It is also contemplated that a lens can be installed at the optical fiber input for optimizing the coupling of the reference beam into the optical fiber.

Mie calculations show that the 176°–178° scattering integral actually sensed by the nephelometer is an excellent proxy for 180° backscatter for a broad range of particle size distributions and refractive indices (see FIGS. 4A and 4B). Accuracies are about ±2% for the accumulation mode shown in FIG. 4A, and ±10% for the coarse mode shown in FIG. 4B, based on Mie calculations for log normal particle size distributions as shown in these Figures. Test cases used geometric standard deviations ranging from 1.6 to 2.2 and real refractive indices ranging from 1.36 to 1.52. For the accumulation mode shown in FIG. 4A, volume mean diameter, $D_{gv}$, ranged from about 0.2 to 0.6 μm and single scattering albedo, $\omega_o$, ranged from about 0.77 to about 1.0. For the coarse mode shown in FIG. 4B, $D_{gv}$ ranged from about 1.0 to about 5.0, and $\omega_o$ from about 0.85 to about 1.0 to represent mass dominated by seasalt or mineral dust.

As designed, the system can be selectively run as a 180° nephelometer, using laser 12 as the light source to measure $\beta_p$, or as a normal nephelometer to measure total particulate or aerosol backscatter $\sigma_{sp}$ using a built-in tungsten-halogen lamp 76, as shown in FIG. 1. When energized and enabled, lamp 76 emits non-coherent light 78 through a window 80 into sample volume 16. Ideally, electronically controlled shutters 66 and 68 would be controlled by a mode switch 70 for rapid, automatic switching between the two modes, so that $\beta_p$ and $\sigma_p$ can alternately be measured with nephelometer 10, although manual switching between light sources is possible with the current design. The mode switch, laser 12, lamp 76 (and other components—as appropriate) are connected to a power supply 72. In either case, for a valid comparison of total scatter to 180°-backscatter an assumption would need to be made about the stability of the sampled aerosol with time. For the field data presented herein, the three quantities needed to determine K ($\sigma_{sp}$, $\beta_p$, and $\sigma_{ap}$) were measured simultaneously with three separate instruments, including a conventional nephelometer used to measure $\sigma_{ap}$ and 180° nephelometer 10, which was used to measure $\beta_p$.

Gas Calibration and Noise Measurements

As a closed-volume device, 180° nephelometer 10 is calibrated with gases of known backscatter coefficient. These absolute calibrations can be performed routinely in the field to maintain a record of calibration stability and an analysis of instrumental noise. In this way, detection limits are quantified and performance is continuously monitored. The system has also be calibrated with monodisperse, laboratory generated particles, where the measured 180° backscatter was compared to calculated values using Mie theory.

The basic algorithm for deriving $\beta_p$ from the measured photon counts is:

$$\beta_p = k_2(C - C_{wall}) - \beta_{air}(T,P) \quad (3)$$

where $k_2$ is the calibration slope, C (the instrument signal) is the normalized photon counting rate measured by detector 18, $C_{wall}$ is the calibration offset, which can be interpreted as photon counts associated with scattering off the inside walls, and $\beta_{air}$ is the calculated 180° backscatter coefficient of air at the temperature (T) and pressure (P) measured inside the instrument. The normalized photon counts, C, are corrected for dark counts ($C_{dark}$) and variations in laser brightness and PMT detector sensitivity (via changes in $C_{cal}$):

$$C = \frac{(C_{meas} - C_{dark})}{(C_{cal} - C_{dark})} \quad (4)$$

Rotating chopper disk 48 alternately exposes detector 18 to backscattered photons (through open sector 56), no photons (due to blockage by flat black background sector 52), and a small portion of the laser beam itself (i.e., a portion of reference beam 36 that is diffused by calibration sector 54) to determine $C_{meas}$, $C_{dark}$, and $C_{cal}$, respectively.

The backscatter coefficient of the calibration gases is known to be a function of the refractive index and the molecular anisotropy of the gas as follows:

$$\beta_{gas}(\lambda) = \sigma_{sg}(STP, \lambda) \frac{3}{8\pi} \frac{(1+\gamma)}{(1+2\gamma)} \frac{273.2}{T} \frac{P}{1013.2} \quad (5)$$

where $\sigma_{sg}$ (STP, $\lambda$) is the scattering coefficient at standard temperature and pressure (STP) for a given wavelength, $\gamma$ is a factor accounting for molecular anisotropy, T is the temperature in degrees K, and P is the pressure in hPa. All required parameters are most accurately known for dry air and $CO_2$; thus, these are the calibration gases of choice for most nephelometer applications, including the present invention. For air and $CO_2$, at 532 nm $\sigma_{sg}$(STP)-values are $1.3888 \times 10^{-5}$ and $3.5969 \times 10^{-5}$ (m$^{-1}$), respectively, and $\gamma$-values are 0.01442 and 0.04325, respectively. Thus, $\beta_{air}$ (STP) is $1.63 \times 10^{-6}$ (m$-1$ sr$-1$) and $\beta_{CO2}$(STP) is $4.12 \times 10^{-6}$ (m$^{-1}$ sr$^{-1}$). Given knowledge of the calibration gases, the calibration constants are determined as:

$$k_2 = \frac{(\beta_{CO2} - \beta_{air})}{(C_{CO2} - C_{air})}, \text{ and } C_{wall} = C_{air} - \frac{\beta_{air}}{k_2} \quad (6)$$

Note that $C_{CO2}$ and $C_{air}$ are actually measured over the angular range 176°–178°, whereas the known values, $\beta_{CO2}$ and $\beta_{air}$, are for a 180° scattering angle. Implicit in $k_2$, then, is the conversion from $\sigma_{gas}$, 176°–178° to $\beta_{gas}$. This conversion is carried over with $k_2$ to all other scattering measurements.

A 4-point calibration is performed (using air and $CO_2$ at pressures of 1 and 0.5 atm) of 180° nephelometer 10, which indicates excellent linearity and very small wall scattering. ($C_{wall}$ is less than 5% of C for particle-free air.) In addition, numerous measurements of air and $CO_2$ to study noise levels, mechanical stability, sensitivity to laser beam alignment, etc. have been made These tests yielded calibration constants that varied by <4% under normal working conditions and indicated a detection limit for 5-minute averages of approximately 0.10 times $\beta_{air}$.

The present invention has also been calibrated using monodisperse latex spheres. Because the particles in this experiment are known to be nearly perfectly spherical and very close to monodisperse, their light scattering characteristics, (i.e., $\beta_p$ and $\sigma_{sp}$) can be very accurately calculated using Mie theory. The value $\beta_p$ was measured using 180° backscatter nephelometer 10 and $\sigma_{sp}$ was measured using a conventional integrating nephelometer. Latex spheres are non-absorbing (being white), so $\sigma_{ap}$ is zero; the lidar ratio can thus be calculated directly from the two measured quantities. As shown in FIG. 5, the derived values of K are in excellent agreement with that predicted by Mie theory, proving that the 180° backscatter nephelometer is indeed properly measuring $\beta_p$.

Lidar Ratio Measurements

Field measurements of the lidar ratio, K (Equation 2) were made at Cheeka Peak Observatory (CPO), located at 480 m altitude in the far northwest corner of Washington state. This coastal station samples a wide variety of air mass types, including clean marine air (the dominant category), continental air affected by urban/industrial pollution in the Pacific Northwest, and occasionally, polluted air from Asia. Three optical quantities, $\sigma_{sp}$, $\sigma_{ap}$, and $\beta_p$, were measured to calculate K. The first two, to determine $\sigma_{ep}$, were measured with existing conventional instrumentation. Scattering was measured using a conventional integrating nephelometer (TSI Model 3563), and $\sigma_{ap}$ was measured by an absorption photometer that responds to differential transmission of light through a filter (Model PSAP, produced by Radiance Research Inc., Seattle, Wash.) All quantities were measured at a low relative humidity (RH <40%). Impactors were used to alternate every 5 minutes between measuring aerosol with diameter D≦10$\mu$m and aerosol with D≦1 $\mu$m, so both fine and coarse mode data were acquired.

Several adjustments to the nephelometer and absorption photometer measurements were necessary for accurate determination of K. A correction was made for angular non-idealities in the nephelometer measurement of $\sigma_{sp}$ using a technique well known to those of ordinary skill in the art. For the absorption photometer, a conventional calibration and scattering correction was made. Finally, both scattering and absorption were measured at 550 nm wavelength and were adjusted to the 532 nm laser wavelength using a power law relationship as defined by the ångström exponent, å:

$$å(\lambda_1 / \lambda_2) = -\frac{\log\left(\frac{\sigma_{sp}^{\lambda_1}}{\sigma_{sp}^{\lambda_2}}\right)}{\log(\lambda_1 / \lambda_2)} \quad (7)$$

The value of å was empirically determined for $\sigma_{sp}$ by using the 3-wavelength nephelometer scattering measurements at 550 nm and 450 nm. For conversion of $\sigma_{ap}$ from 550 nm to 532 nm, å was assumed to be 1.0. The combined effect of these adjustments is to increase light extinction, $\sigma_{ep}$, by up to 40% relative to its uncorrected value, primarily dueto the correction of the integrating nephelometer for truncation errors for coarse particles. Following these adjustments, the uncertainty in $\sigma_{ep}$ is less than 20% for the Cheeka Peak data set. These corrections are more important for the coarse particle aerosols (e.g. dust, sea salt) and less important for fine particles (e.g. industrial pollution).

Aerosol optical properties were determined during two distinct sampling periods, one continental and one marine. The continental data were separated into two cases to reflect a step-change in aerosol light absorption. The measurement protocol involved separate analysis of sub-1 $\mu$m and sub 10 $\mu$m diameter particles. Analysis of the complete data set reveals that the continental aerosol is dominated by sub-pm particles, while the marine aerosol is dominated by super-μm particles. This finding is confirmed by the contrasting values of å—around two for the continental period and zero for the marine period. The continental aerosol has a significant absorption component, indicative of pollution, whereas the marine aerosol is non-absorbing, consistent with seasalt composition.

The fine-mode dominated continental air has a much higher lidar ratio that the coarse-mode dominated marine air, as is consistent with Mie theory. For the marine case, the lidar ratio is relatively constant, despite large changes in total aerosol amount. In all three cases, the variability in the lidar ratio is ~15%, which is attributed to instrumental noise rather than to real variation in the ambient aerosol lidar ratio. The 180° nephelometer laser stability degraded during the field campaign, significantly affecting the instrument performance. Clean air measurements were used to correct for offset variation, and span gas calibrations were made in close proximity to each sample period. Based on this information, it is estimated that the lidar ratios are typically accurate to within 20%. Improvement in the uncertainty in measurements is expected if the instrument is run with a laser that conforms to the manufacturer stability specification of <1% variation. Still better results should be possible with higher aerosol loads via higher signal-to-noise ratios.

The 180° nephelometer described above, when used with a total-scatter nephelometer and an instrument that measures light absorption, allows for empirical determination of $\beta_p$ and the lidar ratio, obviating the need to rely exclusively on values calculated from Mie theory. Such calculations not only involve uncertainties associated with input size distributions and refractive indices but also rely on assumptions of particle homogeneity and sphericity. The instrument is suitable for routine ground-based monitoring as well as periodic airborne surveys of $\beta_p$ and K. The closed-cell design of 180° nephelometer 10 permits an absolute calibration with gases; therefore, $\beta_p$, can be determined without assumptions about particle shape, composition, or state of mixture.

Initial field results show a sharp contrast between the lidar ratio of polluted continental aerosol (60–70) and clean marine aerosol (~20). Uncertainties in these values are on the order of 20%, largely due to instrumental noise in 180° nephelometer 10. This noise has been traced to low photon counting rates for the reference beam and to erratic behavior of the laser during the field deployment.

Further enhancements to the nephelometer can be undertaken. The current design allows for measurement of both $\beta_p$ and $\sigma_{sp}$ with a single. instrument, via manual switching between the laser and nephelometer lamp light sources or with shutters 66 and 68 synchronized with the reference beam chopper that are placed in front of the laser and the lamp, allowing nearly simultaneous measurement of the two quantities, $\beta_p$, and $\sigma_{sp}$, for example, alternating between the two light sources every one to two seconds. It is also contemplated that these measurements can be made in real time, using a processor 74 (or personal computer) that is coupled to detector 18 and mode switch 70, as shown in. FIG. 1. The processor can employ the photon count determined by the PMT of the detector, coordinated with the light source being used, to determine the values for $\beta_p$ and $\sigma_{sp}$ automatically in real time. The only other parameter that would need to be measure is the value of $\sigma_{ap}$, which can be done with a photometer as described above.

Shape effects may be a dominant source of uncertainty in theoretical determinations of the lidar ratio, especially for coarse mode dust and seasalt particles. The empirical method of determining the lidar ratio could be used to study shape effects and would be enhanced in this regard, by adding a polarization measurement. At present, the instrument measures the sum of polarized plus depolarized scattered light. A second detection channel could be added to measure only the depolarized scattered light. The ratio of these two quantities (the depolarization ratio) should be a sensitive indicator of non-sphericity.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for measuring a backscatter coefficient for an aerosol entrained in a fluid, comprising:
   (a) a housing defining a chamber having an inlet port through which a fluid enters the chamber, and an outlet port through which the fluid exits the chamber, an interior of said housing being covered with an optically light absorptive coating that provides minimal light reflection;
   (b) a light detector disposed within the housing, said light detector producing an output signal indicative of an intensity of light incident on the light detector;
   (c) a plurality of light baffles disposed between the light detector and the chamber, said baffles defining an optical sensing path of limited scope for the light detector extending from within the chamber to the light detector so that only light traveling along said optical sensing path toward the light detector is detected by the light detector; and
   (d) a coherent light source that produces a beam of coherent light directed away from the light detector at an acute angle relative to a central axis of the optical sensing path, so that coherent light reflected from said aerosol within the chamber travels back along the optical sensing path and is detected by the light sensor, the signal produced by the light detector in response thereto being indicative of the backscatter coefficient for the aerosol.

2. The apparatus of claim 1, wherein the acute angle is less than 4 degrees.

3. The apparatus of claim 1, further comprising:
   (a) a rotating chopper disk that includes a plurality of sectors having different optical properties that are selectively positionable in the optical sensing path, including:
      (i) an open sector through which light freely travels;
      (ii) a light absorbing sector that blocks and absorbs substantially all light incident upon it; and
      (iii) a calibration sector that transmits only a predefined small portion of the light incident upon it and diffuses the light that is thus transmitted over a large area so that only a portion travels along the optical sensing path; and
   (b) a partially reflecting surface disposed to reflect a portion of the coherent light produced by the coherent light source along a different path than a remainder of the coherent light, forming a reference beam, said reference-beam being directed toward the chopper disk at an angle so that the reference beam does not travel directly along the optical sensing path toward the light detector when passing through the open sector, and so that when the reference beam is directed at the calibration sector, only a portion of the reference beam is diffused thereby to travel toward the light detector along the optical sensing path, said portion of the reference beam that is detected by the light detector causing the light detector to produce a signal that is indicative of an intensity of the coherent light source, to compensate for variations in said intensity in determining the backscatter coefficient for the aerosol.

4. The apparatus of claim 1, further comprising at least one baffle disposed within the chamber to minimize reflected light from any surface traveling along the optical sensing path toward the light detector.

5. The apparatus of claim 1, further comprising a light absorption surface toward which the beam of coherent light is directed, said beam of coherent light striking the light absorption surface at a point that is outside the optical sensing path to minimize any reflected light traveling back toward the light detector along the optical sensing path.

6. The apparatus of claim 1, further comprising a non-coherent light source that is selectively enabled to transmit light into the chamber in a direction generally transverse to the optical sensing path during a time interval when said coherent light source is selectively disabled from transmitting coherent light into the chamber, light produced by the non-coherent light source that is reflected from the aerosol toward the light detector along the optical sensing path causing the signal of the light detector to be indicative of light extinction due to total light scattering by the aerosol.

7. The apparatus of claim 6, further comprising electronically controlled shutters disposed between the chamber and the coherent and non-coherent light sources to selectively block light produced by the coherent light source and the non-coherent light source, during alternate time intervals.

8. A method for measuring a lidar ratio of an aerosol entrained in a fluid, comprising the steps of:

(a) providing a light detector in a housing through which the fluid and the aerosol are circulated, and a coherent light source;

(b) transmitting a beam of coherent light produced by the coherent light source substantially along an optical sensing path of the light detector, but directed away from the light detector, said beam of coherent light being directed along a path that deviates from a central axis of the optical sensing path by only a small acute angle;

(c) detecting light scattered by the aerosol particles back along the optical sensing path with the light detector, producing a signal determinative of light backscattering by the aerosol;

(d) measuring light extinction due to total light scattering by the aerosol;

(e) measuring light absorption of the aerosol; and (f) determining the lidar ratio of the aerosol as a function of the light backscattering, light extinction due to total light scattering, and light absorption by the aerosol.

9. The method of claim 8, wherein the lidar ratio is equal to the sum of the light extinction due to scattering and the light absorption of the aerosol divided by the light backscattering of the aerosol.

10. The method of claim 8, wherein the small acute angle by which the boam of coherent light deviates from the central axis of the optical sensing path is less than 4 degrees.

11. The method of claim 8, wherein the signal produced by the light detector is substantially indicative of 180 degree light backscattering for the aerosol.

12. The method of claim 8, further comprising the step of compensating the determination of light backscattering for variations in an intensity of the beam of coherent light.

13. The method of claim 8, further comprising the steps of periodically determining a background noise level of the light detector when substantially no light is incident upon it; and compensating the determination of the light backscattering of the aerosol for the background noise level of the light detector.

14. The method of claim 8, further comprising the step of calibrating the light detector with an aerosol having a known light backscattering characteristic.

* * * * *

UNITED STATES PATENT AND TRADEMARK OFFICE
CERTIFICATE OF CORRECTION

PATENT NO. : 6,404,494 B1
DATED : June 11, 2002
INVENTOR(S) : Masonis et al.

It is certified that error appears in the above-identified patent and that said Letters Patent is hereby corrected as shown below:

<u>Title page,</u>
Please add the following section heading and paragraph:
-- Government Rights
This invention was made with government support under Grant Number NAG 1 1877 awarded by NASA, and the government has certain rights to the invention. --
Item [56], References Cited, U.S. PATENTS,
"4,871,251      10/1989      Priekschat et al." should read
-- 4,871,251      10/1989      Preikschat et al. --

<u>Column 2,</u>
Line 5, "$\sigma_p$" should read -- $\sigma_{ep}$ --
Line 23, ".dust" should read -- dust --

<u>Column 3,</u>
Line 50, "this." should read -- this --

<u>Column 6,</u>
Line 28, "the." should read -- the --
Line 46, "selectively." should read -- selectively --

<u>Column 7,</u>
Line 1, "aerosolparticles" should read -- aerosol particles --

<u>Column 10,</u>
Line 44, "$\sigma_p$" should read -- $\sigma_{sp}$ --
Line 65, "be" should read -- been --

<u>Column 11,</u>
Line 62, "made" should read -- made. --

<u>Column 12,</u>
Line 54, "dueto" should read -- due to --
Line 67, "sub-pm" should read -- sub-$\mu$m --

<u>Column 13,</u>
Line 58, "in." should read -- in --
Line 63, "measure" should read -- measured --

UNITED STATES PATENT AND TRADEMARK OFFICE
CERTIFICATE OF CORRECTION

PATENT NO. : 6,404,494 B1
DATED : June 11, 2002
INVENTOR(S) : Masonis et al.

It is certified that error appears in the above-identified patent and that said Letters Patent is hereby corrected as shown below:

Column 14,
Line 66, "reference-beam" should read -- reference beam --

Column 16,
Line 23, "boam" should read -- beam --

Signed and Sealed this

Eleventh Day of February, 2003

JAMES E. ROGAN
*Director of the United States Patent and Trademark Office*